(12) United States Patent
Monteiro et al.

(10) Patent No.: US 10,025,000 B2
(45) Date of Patent: Jul. 17, 2018

(54) OPTICAL SENSORS FOR DOWNHOLE TOOLS AND RELATED SYSTEMS AND METHODS

(71) Applicant: Baker Hughes Incorporated, Houston, TX (US)

(72) Inventors: Othon R. Monteiro, Houston, TX (US); Radhika Suresh, Sugar Land, TX (US)

(73) Assignee: Baker Hughes Incorporated, Houston, TX (US)

( * ) Notice: Subject to any disclaimer, the term of this patent is extended or adjusted under 35 U.S.C. 154(b) by 235 days.

(21) Appl. No.: 15/003,578

(22) Filed: Jan. 21, 2016

(65) Prior Publication Data
US 2017/0212272 A1    Jul. 27, 2017

(51) Int. Cl.
*E21B 49/08* (2006.01)
*G01V 8/16* (2006.01)
(Continued)

(52) U.S. Cl.
CPC ............... *G01V 8/16* (2013.01); *E21B 49/08* (2013.01); *G01N 33/0044* (2013.01);
(Continued)

(58) Field of Classification Search
CPC ..... E21B 2049/085; E21B 49/08; G01V 8/16; G01N 33/0044; G01N 33/24; G01N 21/63;
(Continued)

(56) References Cited

U.S. PATENT DOCUMENTS

| 5,304,492 A | 4/1994 | Klinkhammer |
|---|---|---|
| 6,020,207 A | 2/2000 | Liu |

(Continued)

FOREIGN PATENT DOCUMENTS

| EP | 2392917 A1 | 12/2011 |
|---|---|---|
| WO | 03030621 A2 | 4/2003 |

OTHER PUBLICATIONS

Zhang et al. ACS Appied Materials and Interfaces, vol. 6, Apr. 22, 2014, pp. 6300-6307.*

(Continued)

*Primary Examiner* — Maureen Wallenhorst
(74) *Attorney, Agent, or Firm* — TraskBritt (57) ABSTRACT

A method of detecting at least one of an analyte or a condition of a fluid within a subterranean formation includes operably coupling a radiation source to at least one optical fiber coupled to a sensor having optically sensitive materials including at least one of chromophores, fluorophores, metal nanoparticles, or metal oxide nanoparticles dispersed within an optically transparent permeable matrix material. The sensor is contacted within a wellbore with a fluid and the fluid is passed through at least a portion of the sensor. Electromagnetic radiation is transmitted from the radiation source through at least one optical fiber to the sensor and at least one of an absorbance spectrum, an emission spectrum, a maximum absorption intensity, or a maximum emission intensity of electromagnetic radiation passing through the sensor after contacting at least some of the optically sensitive materials with the fluid is measured. Additional methods of determining a concentration of hydrogen sulfide in a fluid within a subterranean formation and related downhole optical sensor assemblies are disclosed.

20 Claims, 6 Drawing Sheets

(51) Int. Cl.
*G01N 33/24* (2006.01)
*G01N 21/64* (2006.01)
*G01N 33/00* (2006.01)

(52) U.S. Cl.
CPC ...... *E21B 2049/085* (2013.01); *G01N 21/643* (2013.01); *G01N 33/24* (2013.01); *Y10T 436/184* (2015.01)

(58) Field of Classification Search
CPC .... G01N 21/64; G01N 21/643; Y10T 436/18; Y10T 436/182; Y10T 436/184; Y10T 436/255; Y10T 436/25875
USPC ....... 436/25, 28, 80, 84, 119, 121, 164, 165, 436/167, 172, 178, 181; 422/82.05, 422/82.08, 82.09 Q
See application file for complete search history.

(56) References Cited

U.S. PATENT DOCUMENTS

| | | | |
|---|---|---|---|
| 6,507,401 | B1 | 1/2003 | Turner et al. |
| 6,939,717 | B2 | 9/2005 | Jiang et al. |
| 6,995,360 | B2 | 2/2006 | Jones et al. |
| 7,025,138 | B2 | 4/2006 | Kurkjian et al. |
| 7,231,819 | B2 | 6/2007 | Jones et al. |
| 7,251,384 | B2 | 7/2007 | da Silva Junior et al. |
| 7,395,704 | B2 | 7/2008 | DiFoggio |
| 7,423,258 | B2 | 9/2008 | DiFoggio et al. |
| 7,516,654 | B2 | 4/2009 | DiFoggio |
| 7,814,782 | B2 | 10/2010 | DiFoggio |
| 7,835,003 | B2 | 11/2010 | Jiang et al. |
| 7,959,864 | B2 | 6/2011 | Jiang et al. |
| 8,039,791 | B2 | 10/2011 | Dong et al. |
| 8,268,146 | B2 | 9/2012 | Jiang et al. |
| 8,379,207 | B2 | 2/2013 | DiFoggio et al. |
| 2006/0043304 | A1 | 3/2006 | Miller et al. |
| 2008/0245960 | A1 | 10/2008 | Csutac |
| 2009/0137054 | A1* | 5/2009 | Hoagland ............... B82Y 30/00 436/102 |
| 2010/0050761 | A1 | 3/2010 | Lawrence et al. |
| 2010/0091288 | A1* | 4/2010 | DiFoggio ............. G01N 21/783 356/436 |
| 2011/0104809 | A1* | 5/2011 | Jiang ....................... C09K 8/52 436/25 |
| 2012/0137764 | A1 | 6/2012 | Lawrence et al. |
| 2012/0280144 | A1 | 11/2012 | Guilfoyle et al. |
| 2013/0056626 | A1 | 3/2013 | Shen et al. |
| 2013/0245947 | A1* | 9/2013 | Samsom ................. E21B 47/10 702/6 |
| 2014/0138259 | A1* | 5/2014 | Mickelson ......... G01N 33/0044 205/775 |
| 2014/0318769 | A1 | 10/2014 | Walton et al. |
| 2015/0167458 | A1* | 6/2015 | Harms ................. E21B 49/081 166/250.11 |
| 2016/0178793 | A1* | 6/2016 | Vijayakumar ......... G01N 21/39 356/409 |

OTHER PUBLICATIONS

International Search Report for International Application No. PCT/US2017/013905 dated Apr. 19, 2017, 3 pages.
International Written Opinion for International Application No. PCT/US2017/013905 dated Apr. 19, 2017, 10 pages.
Chen et al., Reaction-Based Genetically Encoded Fluorescent Hydrogen Sulfide Sensors, Journal of the American Chemical Society, vol. 134, (2012), pp. 9589-9592.
Chen et al., A Red Amission Flourorescent Probe for Hydrogen Sulfide and its Application in Living Cells Imaging, Tetrahedron Letters, vol. 54, (2013), pp. 2980-2982.
Creek et al., Downhole Fluids Laboratory, Oilfield Review 21, No. 4, Winter 2009/2010, pp. 38-54.
Elsayed et al., Azide and Sulfonylazide Functionalized Fluorophores for the Selective and Sensitive Detection of Hydrogen Sulfide, Sensors and Actuators vol. B 207, (2015), pp. 987-994.
Kanan et al., Semiconductor Metal Oxide Based Sensors for Selective Gas Pollutant Detection, Sensors, vol. 9, (2009, (pp. 8158-8196.
Montoya et al., Development of Selective Colorimetric Probes for Hydrogen Sulfide Based on Nucleophilic Aromatic Substitution, The Journal of Organic Chemistry, vol. 78, (2013), pp. 6550-6557.
Montoya et al., Hydrogen Sulfide Deactivates Common Nitrobenzofuazan-Based Fluorescent Thiol Labeling Reagents, Analytical Chemistry, vol. 86, (2014), pp. 6032-6039.
Rodriguez-Fernandez et al., Optical Fibre for Hydrogen Sulphide Monitoring in Mouth Air, Analytic Chimica Acta, vol. 471, (2002), pp. 13-23.
Wallace et al., A Colorimetric Response to Hydrogen Sulfide, Sensors and Actualtory vol. B 120, (2007), pp. 362-367.
Yuan et al., Reaction-Based Fluorescent Probe for Hydrogen Sulfide with Large Signal-to-Noise Ration in Living Cells and Tissues, Sensors and Actuators, vol. B 196, (2014), pp. 151-155.
Yusof et al., A Flow-Through Optical Fibre Reflectance Sensor for the Detection of Lead Ion Based on Immobilised Gallocynine, Sensors and Actuators vol. B 94, (2003), pp. 201-209.

* cited by examiner

OPTICAL SENSORS FOR DOWNHOLE TOOLS AND RELATED SYSTEMS AND METHODS

TECHNICAL FIELD

Embodiments of the disclosure relate generally to optical sensors for use downhole, and to methods of using such optical sensors in conjunction with forming, enlarging, or maintaining a wellbore, as well as in production of hydrocarbons from subterranean formations.

BACKGROUND

Drilling fluids are used in the drilling of subterranean oil and gas wells. In rotary drilling, drilling fluids, also known as "drilling muds," or simply "muds" due to a high solids content, are used for cooling and lubricating drill bits, lubricating drill pipes, carrying cuttings and other materials from a borehole to the surface of the earth, and exerting a hydrostatic pressure against the borehole wall to prevent the flow of fluids from the surrounding formation into the borehole. However, drilling fluids can become contaminated by compounds encountered during drilling operations.

For example, gases commonly encountered in subterranean formations include methane ($CH_4$), carbon dioxide ($CO_2$), carbon monoxide (CO), nitrogen ($N_2$), ammonia ($NH_3$), and hydrogen sulfide ($H_2S$), which may be dissolved within fluids within the subterranean formation. Some of the gases have negative effects on drill string components, and may impose additional costs in conducting drilling operations in such environments. For example, $H_2S$ is toxic, flammable, and corrosive. In certain concentrations, and over time, $CO_2$ may be corrosive to processing equipment by reacting with steel.

In addition to drilling fluids, other fluids within the wellbore, such as stimulation fluids, workover fluids, production fluids, etc., may include corrosive gases or other materials that may induce corrosion or otherwise damage the downhole equipment.

Conventional methods of measuring a concentration of such detrimental components within the wellbore include obtaining samples of the fluids within the wellbore and analyzing the fluids at the surface. However, samples acquired at high-temperature and high-pressure (HPHT) conditions encountered downhole may not exhibit the same properties at the surface as they exhibit in the downhole environment. For example, laboratory analysis typically occurs after downhole samples have been flashed to room temperature and pressure conditions. The temperature and pressure reductions, however, cause precipitation of solids from the fluids, altering a pH of the sample. In addition, the temperature and pressure reductions may cause acidic gases such as $CO_2$ and $H_2S$ to come out of solution, increasing a pH of the laboratory sample. Further, downhole samples that are analyzed at the surface may not be an accurate representation of the constituencies of fluids within particular zones of the subterranean formation. For example, fluids produced at the surface may be a mixture of fluids located within distinct zones of the subterranean formation and, therefore, may not be an accurate representation of the fluids located within distinct zones of the subterranean formation.

BRIEF SUMMARY

Embodiments disclosed herein include downhole optical sensors for detecting an analyte or condition of a wellbore fluid, as well as related methods. For example, in accordance with one embodiment, a method of detecting at least one of an analyte or a condition of a fluid within a subterranean formation comprises operably coupling a radiation source to at least one optical fiber coupled to a sensor comprising optically sensitive materials including at least one of chromophores, fluorophores, or metal nanoparticles dispersed within an optically transparent porous matrix material, contacting the sensor within a wellbore with a fluid and passing the fluid through at least a portion of the sensor, transmitting electromagnetic radiation from the radiation source through at least one optical fiber to the sensor, and measuring at least one of an absorbance spectrum, an emission spectrum, or a maximum absorption intensity of electromagnetic radiation passing through the sensor after contacting at least some of the optically sensitive materials with the fluid.

In additional embodiments, a method of determining a concentration of hydrogen sulfide in a fluid within a subterranean formation comprises locating a sensor comprising optically sensitive materials comprising at least one of chromophores, fluorophores, and nanoparticles dispersed within a porous silica matrix material proximate at least one component of downhole equipment in a wellbore extending through one or more subterranean formations, the sensor operably coupled through at least one fiber optic cable to a radiation source configured to provide electromagnetic radiation to the sensor, contacting the sensor with a fluid within at least one of the downhole equipment or the wellbore, transmitting electromagnetic radiation from the radiation source through the sensor and to a detector operably coupled to the fiber optic cable, and determining, with the detector, a change in an optical characteristic of at least one of the optically sensitive materials of the sensor responsive to contact of the sensor with the fluid.

In further embodiments, a downhole optical sensor assembly comprises a sensor operably coupled to at least one component of downhole equipment, the sensor including optically sensitive materials comprising one of chromophores, fluorophores, or metal nanoparticles disposed within a porous optically transparent matrix material, a radiation source coupled to the sensor through a fiber optic cable, the radiation source configured to generate electromagnetic radiation for transmission through at least one optical fiber of the fiber optic cable, and a detector coupled to the sensor through a fiber optic cable, the detector configured to measure at least one of an absorbance spectrum, an emission spectrum, or a maximum absorption intensity of electromagnetic radiation passing through the sensor.

DETAILED DESCRIPTION

Illustrations presented herein are not meant to be actual views of any particular material, component, or system, but are merely idealized representations that are employed to describe embodiments of the disclosure.

The following description provides specific details, such as material types, compositions, material thicknesses, and processing conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional techniques employed in the industry. In addition, the description provided below does not form a complete process flow for detecting a concentration of an analyte or a condition of a fluid within a subterranean formation, or to related optical sensor assemblies. Only those process acts and structures necessary to understand the embodiments of the disclosure are described in detail below. A person of ordinary skill in the art will understand that some process components (e.g., fiber optic cables, optical fibers, processors, pipelines, line filters, valves, temperature detectors, flow detectors, pressure detectors, and the like) are inherently disclosed herein and that adding various conventional process components and acts would be in accord with the disclosure. Additional acts or materials to determine a concentration of an analyte or another condition of a wellbore fluid with a downhole sensor may be performed by conventional techniques.

As used herein, an "optical property" means and includes any measurable property relating to absorption, reflection, refraction, fluorescence, emission, and transmittance of electromagnetic radiation (e.g., light) through a material. As nonlimiting examples, optical properties include a wavelength at which a material exhibits a peak absorption intensity, a wavelength at which a material exhibits a peak emission intensity, a wavelength at which a material exhibits a peak fluorescence intensity (e.g., a color of light emitted during fluorescence, such as when the fluorescence is in the visible spectrum), an excitation spectrum, an emission spectrum, a fluorescence spectrum, an intensity of absorbed electromagnetic radiation, an intensity of emitted electromagnetic radiation, and a shift in a wavelength of a peak absorption intensity. The electromagnetic radiation may be anywhere within the electromagnetic spectrum, including, for example, the UV spectrum, the visible spectrum, and the infrared (IR) spectrum.

Methods and optical sensors as disclosed herein may be used for detecting one or more of a concentration of an analyte in a fluid, or a condition (e.g., a pH, a salinity, etc.) of the fluid, in situ (e.g., within subterranean formations at temperatures and pressures encountered within the subterranean formations). For example, a fluid used or encountered in a subterranean formation may be analyzed without transporting the fluid to the surface. Accordingly, the fluid may be analyzed in situ without reducing a temperature or pressure of the fluid to atmospheric conditions that may be encountered at the surface, such as in a laboratory. The methods may generally include passing a liquid including an analyte of interest adjacent an optical sensor and sensing one or more optical properties of the optical sensor responsive to passing the liquid adjacent the optical sensor. The optical sensor may be located at a downhole location, such as within a wellbore extending through one or more subterranean formations. As used herein, the terms "sensor" and "optical sensor" may be used interchangeably.

The fluid to be analyzed may include, for example, a production fluid, a drilling fluid, a stimulation fluid, a workover fluid, etc. As used herein, a "downhole fluid" means and includes one or more of a production fluid, a drilling fluid, a stimulation fluid, a workover fluid, or other fluid that may be encountered within a wellbore. The terms "fluid" and "downhole fluid" may be used interchangeably herein.

A sample of the fluid may be transferred to the optical sensor where one or more components (e.g., analytes) of the fluid may be analyzed. The optical sensor may be located at a downhole location. The sensor may be configured to determine a concentration of hydrogen sulfide ($H_2S$) in the fluid, a concentration of lead in the fluid, a pH of the fluid, or a concentration of another analyte of interest or another condition of the fluid. In some embodiments, the sensor includes optically sensitive materials or precursors to optically sensitive materials embedded within a substantially transparent and porous matrix material. The matrix material may comprise an open pore network such that fluid may flow through the pores of the open pore network and contact the optically sensitive materials dispersed throughout the matrix material. Responsive to contacting the sensor, at least a component of the fluid, such as the analyte of interest, may interact with (e.g., react with, chemically adsorb, physically adsorb, etc.) the optically sensitive materials, altering optical properties of the sensor. Detection of one or more properties of electromagnetic radiation passing through the sensor may correspond to a presence, a concentration, or both a presence and concentration, of an analyte of interest or one or more conditions of the fluid (e.g., a pH of the fluid).

Figure 1:
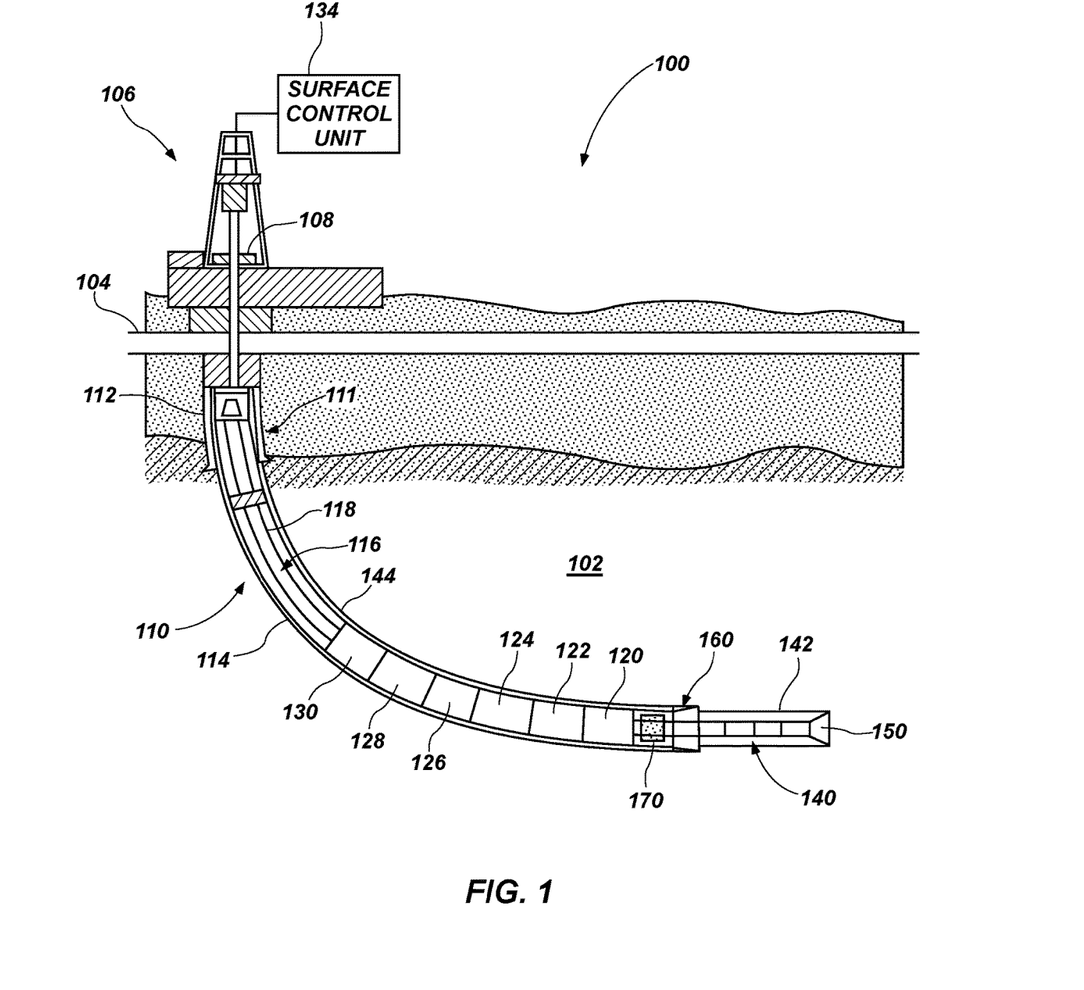
FIG. 1 is a schematic diagram of a wellbore system comprising a drill string that includes a sensor assembly according to an embodiment of the disclosure.

FIG. 1 is a schematic diagram showing a drilling system 100 utilizing the apparatus and methods disclosed herein. FIG. 1 shows a wellbore 110 that includes an upper section 111 with a casing 112 installed therein and a lower section 114 that is being drilled with a drill string 116. The drill string 116 includes a tubular member 118 that carries a drilling assembly 140 (e.g., a bottomhole assembly) at a distal end thereof. The tubular member 118 may be made up by joining drill pipe sections in an end-to-end configuration, or may be coiled tubing. A drill bit 150 (also referred to as a "pilot bit") is attached to the bottom end of the drilling assembly 140 for drilling a first, smaller diameter borehole 142 in a subterranean formation 102. A hole enlargement device 160 (e.g., a reamer) may be placed above or uphole of the drill bit 150 in the drill string 116 to enlarge the smaller diameter borehole 142 to a second, larger diameter borehole 144. The terms wellbore and borehole are used synonymously herein.

The drilling assembly 140 may include, as nonlimiting examples, the drill bit 150, a drilling motor 120, a steering device 122, a sensor sub 124, a bidirectional communication and power module (BCPM) 126, a stabilizer 128, a formation evaluation (FE) module 130, the hole enlargement device 160, and one or more sensor assemblies 170. The drilling assembly 140 may be rotated within the wellbore 110 using the drilling motor 120. The drilling motor 120 may comprise, for example, a hydraulic Moineau-type motor having a shaft, to which the drilling assembly 140 is coupled, that may be caused to rotate by pumping fluid (e.g., drilling mud or fluid) from a surface 104 of the subterranean formation 102 down through a center of the drill string 116, through the drilling motor 120, out through nozzles in the drill bit 150, and back up to the surface 104 through the annular space between the outer surface of the drill string 116 and the exposed surface of the formation within the wellbore 110 (or the exposed inner surface of any casing 112 within the wellbore 110). Alternatively, the drilling assembly 140 may be rotated within the wellbore 110 by rotating the drill string 116 from the surface 104 of the subterranean formation 102, such as with a rotary table 108 or top drive.

The drill string 116 extends to a rig 106 at the surface 104. Although the rig 106 illustrated is a land rig, the rig 106 may include an offshore rig used for drilling underwater. The rig 106 may also include conventional devices, such as mechanisms to add additional sections to the tubular member 118 as the wellbore 110 is drilled. A surface control unit 134, which may be a computer-based unit, is placed at the surface 104 for receiving and processing downhole data transmitted by the drilling assembly 140 and for controlling the operations of the various devices and the sensor assemblies 170 in the drilling assembly 140.

The sensor assemblies 170 may be positioned and configured to directly contact wellbore fluids such as, for example, drilling fluids, production fluids, workover fluids, stimulation fluids, or other fluids that may come into contact with wellbore equipment. The wellbore fluids may include one or more analytes of interest (e.g., $H_2S$, lead, etc.) or may exhibit one or more conditions of interest (e.g., a pH). The sensor assemblies 170 may be configured to interact with one or more materials within the wellbore fluids and may exhibit at least one unique optical property responsive to such exposure. The at least one optical property exhibited by the sensor assemblies 170 exposed to the fluids may correspond to a concentration of one or more analytes within the fluid or a condition of the fluid.

Figure 2A:
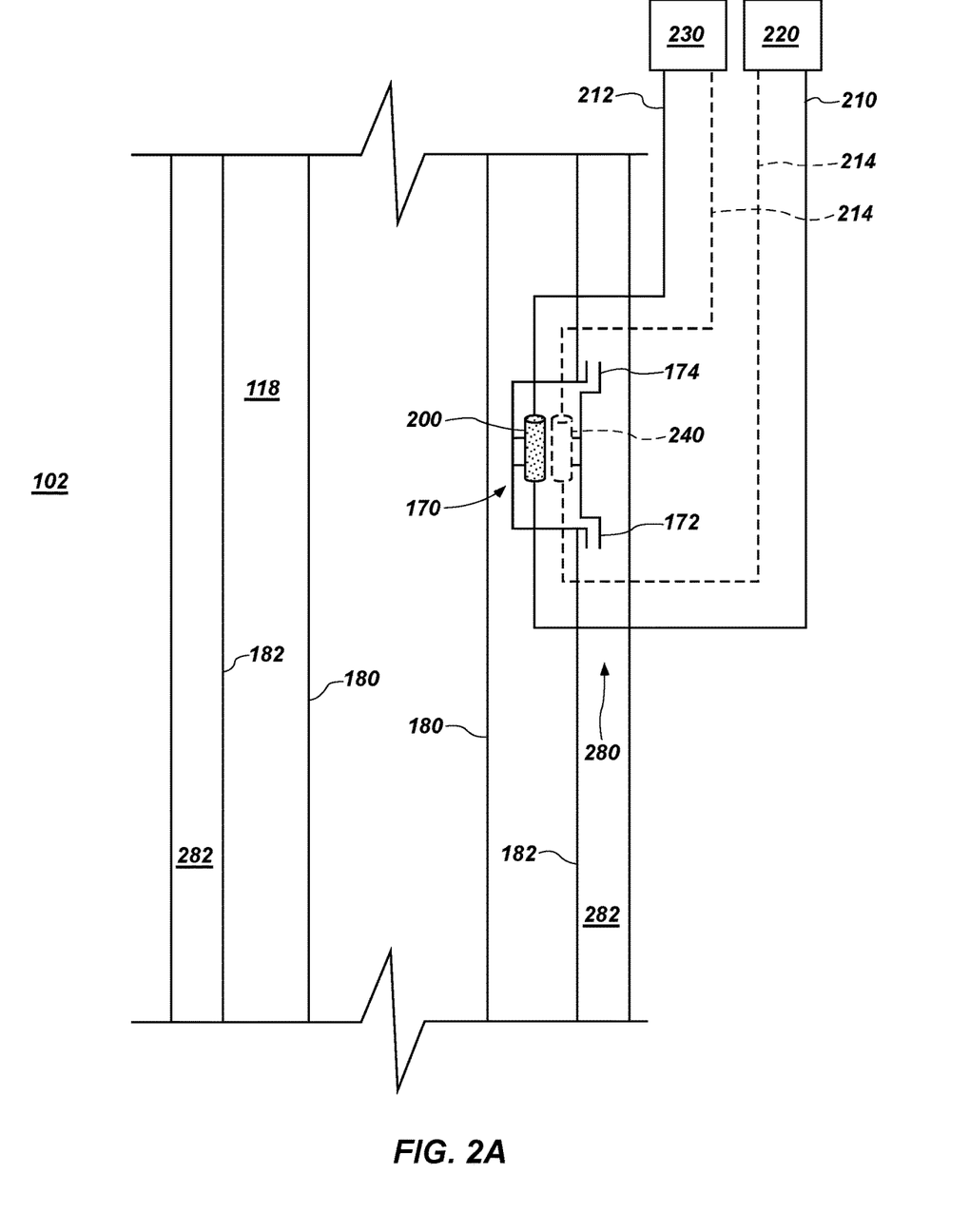
FIG. 2A is a simplified schematic of a portion of a drill string including a sensor assembly according to an embodiment of the disclosure.

FIG. 2A illustrates a simplified schematic of a portion of the tubular member 118 (e.g., a portion of the drill string 116 (FIG. 1), a portion of a production string, etc.) in which the sensor assembly 170 is disposed, according to embodiments of the disclosure. In some embodiments, the sensor assembly 170 may be a part of a drill string sub, such as the sensor sub 124 (FIG. 1). The sensor assembly 170 may be disposed within a portion of the tubular member 118, such as between an inner wall 180 and an outer wall 182 thereof. In some embodiments, drilling fluid may flow in an annular space 282 defined between the outer wall 182 of the tubular member 118 and an exposed surface (e.g., the larger diameter borehole 144) of the subterranean formation 102 within the wellbore 110 in the direction indicated by arrow 280. The fluid may flow to the sensor assembly 170 through, for example, a fluid inlet 172, and may exit the sensor assembly 170 through, for example, a fluid outlet 174. A sensor 200 within the sensor assembly 170 may be substantially surrounded by and in contact with the fluid. Although the fluid inlet 172 and the fluid outlet 174 are illustrated as being configured to sample fluid from the annular area, in other embodiments, the fluid inlet 172 and the fluid outlet 174 may be configured to sample fluid from within the drill string 116, such as when production fluid flows through the tubular member 118.

The sensor assembly 170 includes an optical fiber 210 coupled at a first end to a radiation source 220 and coupled to a sensor 200 at a second end thereof. Another optical fiber 212 may couple the sensor 200 to a detector 230. Although not show in FIG. 2A for clarity, the radiation source 220 and the detector 230 may be located within the tubular member 118, such as between the inner wall 180 and the outer wall 182 and may comprise a part of a drill string sub, such as the sensor sub 124 (FIG. 1). The optical fiber 210 and the another optical fiber 212 may extend between the radiation source 220, the detector 230, and the sensor assembly 170 within the tubular member 118. In other embodiments, each of the radiation source 220 and the detector 230 may be located at a position outside the wellbore 110, such as at the surface 104 (FIG. 1) of the subterranean formation 102 and may be coupled to the sensor 200 through the optical fiber 210 and the another optical fiber 212.

Each of the optical fiber 210 and the another optical fiber 212 may be carried within the tubular member 118, for example, a fiber optic cable. The fiber optic cable may extend along an interior of the tubular member 118, similar to a wireline, as is known to those of ordinary skill in the art, and may be run into the tubular member 118 as desired, or permanently deployed within a wall of the tubular member 118. In other embodiments, fiber optic cable may be located at any suitable location within the drilling system 100 relative to the tubular member 118. For example, the fiber optic cable may be run along an exterior of the tubular member 118, or comprise part of a self-contained sensor package configured for wireless communication.

The radiation source 220 may be configured to provide electromagnetic radiation at a substantially monochromatic (e.g., substantially fixed and uniform) wavelength to the sensor 200. The substantially monochromatic wavelength may be any wavelength in the electromagnetic spectrum. In some embodiments, the monochromatic wavelength is within the visible spectrum of light (e.g., about 380 nm to about 750 nm). In other embodiments, the radiation source 220 includes a broadband radiation source configured to provide the electromagnetic radiation at more than one wavelength (e.g., polychromatic wavelengths). By way of nonlimiting example, the radiation source 220 may include a light-emitting diode (LED) (e.g., a collimated LED, an uncollimated LED), a laser, a xenon lamp, a mercury lamp, or other suitable electromagnetic radiation source.

The electromagnetic radiation may be transmitted to the sensor 200 through the optical fiber 210. At least a portion of the radiation that is transmitted from the radiation source 220 to the sensor 200 may be absorbed by materials within the sensor 200, and at least a portion of the radiation may pass through the sensor 200. For example, the sensor 200 may include one or more optically sensitive materials or precursors to optically sensitive materials (e.g., materials formulated and configured to react with the fluid and form reaction products exhibiting one or more unique optical properties) that may absorb, attenuate, or otherwise interact with the electromagnetic radiation. The at least one optical property may include one or more of an absorption intensity, reflection, refraction, an absorbance spectrum, fluorescence, a fluorescence spectrum, a shift in a peak absorption intensity, or other optical property.

Responsive to exposure to the fluid, the sensor 200 may be configured to exhibit the at least one optical property. One or more materials within the fluid may interact with the optically sensitive materials within the sensor 200 to alter optical properties of the electromagnetic radiation passing through the sensor 200. In some embodiments, the fluid may react with the optically sensitive materials of the sensor 200 as the fluid passes through the sensor, forming one or more reaction byproducts exhibiting unique optical properties. In other embodiments, the fluid may physically adsorb or chemically adsorb onto the sensor 200 and alter one or more optical properties of the sensor 200.

The detector 230 may be configured to measure at least one optical property of electromagnetic radiation (e.g., the at least one optical property) transmitted from the sensor 200. The at least one optical property may include one or more of an absorption intensity, reflection, refraction, an absorbance spectrum, a fluorescence intensity, a fluorescence spectrum, or a shift in a peak absorption intensity. The at least one optical property may correspond to, for example, a reaction product of a chemical reaction between an analyte of interest in the fluid and the optically sensitive materials of the sensor 200, chemical or physical adsorption of the fluid onto the sensor 200, or other interactions between the fluid and the sensor 200.

In some embodiments, the detector 230 includes an optical spectrometer (e.g., spectrophotometer, spectrograph, spectroscope, photodetector, etc.) configured to measure absorption of electromagnetic radiation at different wavelengths for fluids passing through the sensor 200. The detector 230 may include a filter array, a grating array, or a combination thereof, each configured to allow radiation of different wavelengths to pass therethrough. In some embodiments, the detector 230 includes a spectrophotometer configured to measure an intensity of electromagnetic radiation (e.g., light) that passes through the sensor 200 and an amount of electromagnetic radiation absorbed by the sensor 200 at different wavelengths.

With continued reference to FIG. 2A, the optical fiber 210 and the another optical fiber 212 may be configured to transmit electromagnetic radiation to and from the sensor 200 without passing through wellbore fluids located outside of the sensor 200. In other words, the optical fiber 210 and the another optical fiber 212 may be directly coupled to the sensor 200.

In some embodiments, the sensor assembly 170 may include a calibration optical fiber 214 coupled to the radiation source 220, an optically transparent matrix material 240, and the detector 230. The optically transparent matrix material 240 may be substantially similar to the sensor 200 except that it may not include the optically sensitive materials that are dispersed within the sensor. The calibration optical fiber 214 and the optically transparent matrix material 240 may be exposed to the fluid within the wellbore 110 (FIG. 1). In some embodiments, the calibration optical fiber 214 and the optically transparent matrix material 240 may be configured to determine attenuation of electromagnetic radiation as it passes through the fluid, which data may be used to calibrate an amount of electromagnetic radiation that is transmitted from the sensor 200 to the detector 230.

The sensor assembly 170 may be located at any location of the tubular member 118 (e.g., any location of the drill string 116 or a production string) where the sensor assembly 170 may contact the fluid within the respective drill string 116 or production string. Thus, although FIG. 2A illustrates the sensor assembly 170 configured to sample fluid located within the annular space between the tubular member 118 and the borehole, the sensor assembly 170 may be configured to sample fluid located within the tubular member 118, such as during production. In other embodiments, the sensor assembly 170 may be located on a surface of the drilling assembly 140 (FIG. 1) or on a portion of the drill bit 150 (FIG. 1).

Figure 2B:
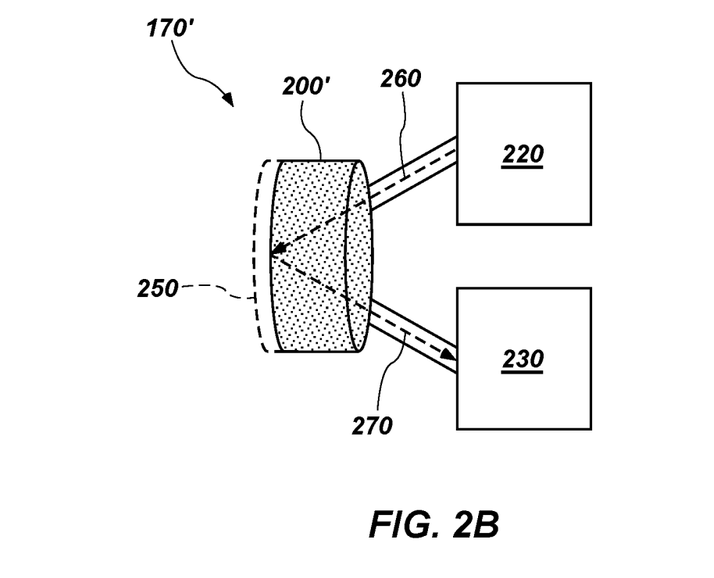
FIG. 2B is a simplified schematic of another sensor assembly according to another embodiment of the disclosure.

FIG. 2B illustrates another sensor assembly 170' that may be used in the drilling assembly 140 (FIG. 1) or other downhole equipment, according to embodiments of the disclosure. The sensor assembly 170' may be similar to the sensor assembly 170 of FIG. 2A, except that in the sensor assembly 170', electromagnetic radiation is reflected from the interfaces of the sensor 200' and detected at the detector 230 rather than being transmitted directly through a first end of the sensor 200 to a second end thereof. The sensor assembly 170' may include a reflective material 250 coupled thereto. Radiation from the radiation source 220, indicated at arrow 260, may be transmitted through the sensor 200' to the reflective material 250. The electromagnetic radiation may be reflected by the reflective material, as indicated at arrow 270. The reflected electromagnetic radiation may be transmitted back through the sensor 200' and to the detector 230.

Although FIG. 2A and FIG. 2B illustrates that the optical fiber 210 and the another optical fiber 212 are different, in some embodiments, the optical fiber 210 and the another optical fiber 212 may comprise the same optical fiber. In some such embodiments, electromagnetic radiation may be pulsed from the radiation source 220 and radiation that is transmitted through the sensor 200 may be transmitted to the detector 230 via the optical fiber.

Figure 3:
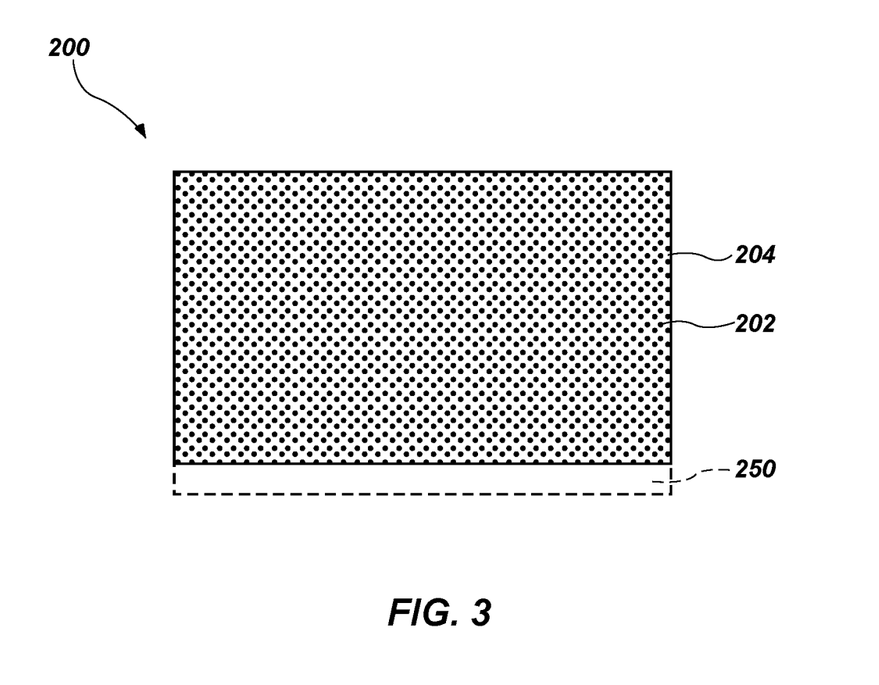
FIG. 3 is a simplified cross-sectional view of a sensor that may be used in the sensor assemblies of FIG. 2A and FIG. 2B.

FIG. 3 illustrates a sensor 200 according to embodiments of the disclosure. The sensor 200 may be disposed within the wellbore 110 (FIG. 1) at a downhole location. As described above with reference to FIG. 2B, a reflective material 250 may be disposed on a side of the sensor 200. The sensor 200 may include one or more optically sensitive materials 202 that are configured to change optical properties responsive to exposure to one or more materials or conditions of the fluid (e.g., an analyte, a fluid of a particular pH, etc.). The optically sensitive materials 202 may be dispersed in a matrix material 204. Thus, the sensor 200 may comprise a nanocomposite material comprising the optically sensitive materials 202 dispersed throughout the matrix material 204.

The matrix material 204 may include an optically transparent material such that electromagnetic radiation (e.g., light) from the radiation source 220 (FIG. 2A, FIG. 2B) may transmit through the matrix material 204 without substantial attenuation. By way of nonlimiting example, the matrix material 204 may include silica glass, borosilicate glass, quartz glass, or other optically transparent materials, such as polymers including polyvinylidene chloride, polyethers, polyacrylates, polysilicones, etc. The plurality of optically sensitive materials 202 may be dispersed within the matrix material 204. The matrix material 204 may be doped with or impregnated with one or more of the optically sensitive materials 202. In some embodiments, the sensor 200 comprises a matrix material 204 having a substantially uniform concentration of the optically sensitive materials 202 dispersed therein.

The matrix material 204 may be permeable to fluids, such as drilling fluids, production fluids, workover fluids, stimulation fluids, etc., such that the fluids may pass through the sensor 200 and contact the optically sensitive materials 202 dispersed therein. The matrix material 204 may include a permeable matrix material with an open pore network to enable the fluid to flow through the pores of the open pore network and contact the optically sensitive materials 202 dispersed throughout the matrix material 204. By way of nonlimiting example, the matrix material 204 may include a porous glass, such as porous silica (e.g., macroporous silica, mesoporous silica, or macroporous silica). A porosity and a mean pore size of the matrix material 204 may be selected such that the fluid may adequately travel through the matrix material 204 and contact the optically sensitive materials 202 dispersed therein. In other words, the matrix material 204 may be selected such that the matrix material 204 is substantially permeable to an analyte of interest.

Each of the optically sensitive materials 202 may be configured to exhibit a unique optical property responsive to interacting with the fluid. Responsive to exposure to the fluid, the plurality of optically sensitive materials 202 may exhibit one or more unique optical properties that are different than optical properties exhibited by the sensor 200 prior to exposure to a particular analyte or condition of the fluid. In some embodiments, the optically sensitive materials 202 may be configured and formulated to react with at least a component of the fluid (e.g., an analyte of interest) and form a reaction product that exhibits one or more unique optical properties. In other embodiments, one or more components of the wellbore fluid may chemically adsorb or physically adsorb onto the optically sensitive materials 202 dispersed throughout the sensor 200. In some such embodiments, the sensor 200 may exhibit one or more unique optical properties responsive to chemical or physical adsorption of at least a component of the fluid to the sensor 200.

In some embodiments, the sensor 200 may be configured to detect a concentration of more than one type of analyte or more than one condition of the fluid. For example, the sensor 200 may include optically sensitive materials 202 configured to detect a concentration of one analyte (e.g., $H_2S$) within the fluid, and other, different, optically sensitive materials 202 formulated and configured to detect a concentration of at least another analyte (e.g., lead) or a condition of the fluid (e.g., a pH of the fluid).

In some embodiments the optically sensitive materials 202 may be loaded into the matrix material 204 at a concentration between about 1 ppm and about 10,000 ppm (i.e., about 1% by weight), such as between about 1 ppm and about 1,000 ppm, between about 10 ppm and about 500 ppm, between about 20 ppm and about 100 ppm, or between about 25 ppm and about 50 ppm. In some embodiments, the concentration of the optically sensitive materials 202 is between about 1 ppm and about 100 ppm. By way of nonlimiting example, the matrix material 204 may be doped with the optically sensitive materials 202 at the time the matrix material 204 is formed, such as during a sol-gel process by which the matrix material 204 is formed.

The optically sensitive materials 202 may include one or more of chromophores, fluorophores (i.e., a compound or particle that re-emits electromagnetic radiation (e.g., light) upon excitation), nanoparticles, or combinations thereof. The optically sensitive materials 202 may include, by way of nonlimiting example, a nitrobenzofurazan compound, (e.g., a chloronitrobenzofurazan such as 4-chloro-7-nitrobenzofurazan), dicyanomethylenedihydrofuran ($C_7H_4N_2O$) (DCDHF), gold nanoparticles, silver nanoparticles, platinum nanoparticles, palladium nanoparticles, copper nanoparticles, zinc oxide (e.g., ZnO), cadmium oxide (e.g., CdO), tungsten oxide (e.g., $WO_3$), tin oxide (e.g., $SnO_2$), copper oxide (e.g., CuO), indium oxide (e.g., $In_2O_3$), iron oxide (FeO, $Fe_2O_3$, $Fe_3O_4$), rhodamine B, a copper(II) chromophore complex (e.g., copper(acetylacetone)(2,9-dimethyl-1,10-phenanthroline)($HNO_3$), Cu(acetylacetone)(4,7-diphenyl-1,10-phenanthroline)($HNO_3$)), dichlorophenolindophenol (e.g., 2,6-dichlorophenolindophenol (DCPI) which may be provided as a Cu(II) complex), m-bromobiamine, one or more fluorophores, and combinations thereof. Nonlimiting examples of suitable fluorophores include an azidophenylalanine (e.g., p-azidophenylalanine), a dansyl azide ($C_{12}H_{12}N_4O_2S$), 7-amino-4-(trifluoromethyl)coumarin or an azide thereof, 4-amino-1-naphthalenesulfonic based (sulfonyl azide), and combinations thereof.

In some embodiments, the optically sensitive materials 202 may be formulated to react with an analyte within the fluid. A reaction product of a reaction between the optically sensitive materials 202 and the analyte may exhibit a unique optical property that may be detected by the detector 230 (FIG. 2A, FIG. 2B) and correlated to a presence and a concentration of the analyte in the fluid. By way of nonlimiting example, the optically sensitive materials 202 may include a nitrobenzofurazan compound that is formulated to react with the fluid, such as with hydrogen sulfide ($H_2S$) within the fluid. A reaction product of the nitrobenzofurazan and $H_2S$ may exhibit different optical properties than $H_2S$, nitrobenzofurazan, or the fluid. In some embodiments, at least a portion of the reaction product may remain in the sensor 200, such as within the matrix material 204, and may alter at least one optical property of electromagnetic radiation passing through the sensor 200. Detection of the optical properties of the reaction product may be an indication of a presence of $H_2S$ within the fluid. In some embodiments, reaction between the optically sensitive materials 202 and the analyte may consume the optically sensitive materials 202. In some such embodiments, the sensor 200 may be configured to provide an indication of when a concentration of an analyte of interest in the fluid exceeds a threshold amount.

In other embodiments, the optically sensitive materials 202 may be configured and formulated such that one or more components within the fluid physically adsorb or chemically adsorb onto the optically sensitive materials 202 within the sensor 200. Thus, materials within the fluid may not chemically react with the optically sensitive materials 202, but rather, may interact with the optically sensitive materials 202 via physical or chemical adsorption. In some such embodiments, interactions between the optically sensitive materials 202 and materials within the fluid may be reversible. Accordingly, sensors 200 with such optically sensitive materials 202 may be configured to operate within the wellbore 110 (FIG. 1) for an extended period of time. In some such embodiments, the optically sensitive materials 202 may include one or more of rhodamine B, a copper(II) chromophore complex (e.g., copper(acetylacetone)(2,9-dimethyl-1,10-phenanthroline)($HNO_3$), Cu(acetylacetone)(4,7-diphenyl-1,10-phenanthroline)($HNO_3$)), dichlorophenolindophenol (e.g., 2,6-dichlorophenolindophenol (DCPI) which may be provided as a Cu(II) complex), m-bromobiamine, or metal nanoparticles, such as nanoparticles of one or more of gold, silver, platinum, palladium, copper, zinc oxide, cadmium oxide, tungsten oxide, tin oxide, copper oxide, indium oxide, or combinations thereof.

In some embodiments, the optically sensitive materials 202 include chromophores, such as one or more of rhodamine B, a copper (II) chromophore complex, copper nanoparticles, 2,6-dichlorophenolindophenol, chloronitrobenzofurazan, or m-bromobiamine.

In embodiments where the optically sensitive materials 202 include metal nanoparticles, the nanoparticles may be substantially spherical and may have a diameter between about 5 nm and about 500 nm, such as between about 5 nm and about 100 nm, or between about 10 nm and about 50 nm. The size of the nanoparticles dispersed within the matrix material 204 may be substantially monodisperse (e.g., substantially all of the nanoparticles may have substantially the same diameter) or polydisperse (e.g., the nanoparticles may have differing diameters).

In some embodiments, the optically sensitive materials 202 include gold nanoparticles. In some such embodiments, the sensor 200 may comprise silica doped with gold nanoparticles. Responsive to exposure to $H_2S$ within the fluid, the sensor 200 including the gold nanoparticles dispersed in a silica matrix may exhibit an increased peak absorbance of the absorbance spectrum of the electromagnetic radiation passing through the sensor 200.

With reference again to FIG. 2A and FIG. 2B, the detector 230 may be configured to detect at least one optical property of one or more reaction products of the optically sensitive materials 202 and at least a component of the fluid, or an optical property of the sensor 200 responsive to interaction with the fluid, such as when one or more chemicals within the fluid are physically adsorbed or chemically adsorbed to the optically sensitive materials 202 of the sensor 200. The at least one optical property may include one or more of a wavelength at which a maximum intensity of electromagnetic radiation is absorbed by the sensor 200, a wavelength at which the sensor 200 exhibits a peak fluorescence intensity, an absorbance spectrum, a fluorescence spectrum, or a shift in a peak absorption intensity of electromagnetic radiation through the sensor 200. The detector 230 may include a filter array configured to measure and detect optical absorption at a particular wavelength, such as at wavelengths that correspond to a presence or concentration of an analyte of interest or a condition of the fluid.

By way nonlimiting example, a wavelength of a maximum electromagnetic absorption through the sensor 200 may correspond to a presence of a reaction product of $H_2S$ within the fluid and the optically sensitive materials 202 within the sensor 200. An intensity at the wavelength of maximum electromagnetic absorption may correspond to a concentration of $H_2S$ (or other analyte) within the fluid. In other embodiments, an absorption intensity at a particular wavelength may correspond to a concentration of $H_2S$ within the fluid. For example, an increasing intensity at a particular wavelength may correspond to an increasing concentration of $H_2S$ within the fluid. In other embodiments, a concentration of $H_2S$ in the fluid may be determined by measuring a wavelength of a maximum absorbance of electromagnetic radiation through the sensor 200. For example, a wavelength of maximum absorbance may increase with increasing concentrations of $H_2S$.

In some embodiments, configuring the sensor assembly 170, 170' (FIG. 2A, FIG. 2B) such that the sensors 200, 200' (FIG. 2A, FIG. 2B) directly contact the fluid and such that electromagnetic radiation passes directly from the optical fiber 210 to the sensors 200, 200' may increase a signal-to-noise ratio and improve detection of the at least one unique optical property of the sensors 200, 200' responsive to interaction with the fluid. By way of contrast, sensor assemblies that are configured such that electromagnetic radiation passes through a fluid medium prior to passing through the sensor may include noise in the obtained signal induced by the presence of impurities or other components in the fluid.

In additional embodiments, a presence and a concentration of additional analytes within the fluid may be determined. For example, a concentration of lead in the fluid may be estimated based on one or more optical properties of the sensor 200 responsive to exposure to the fluid. By way of nonlimiting example, the optically sensitive materials 202 may include one or more of dithizone, diethyldithiocarbamate, 4-(2-pyridilazo)resorcinol, diphenylcarbazone, arsenazo III, 2-(2-thiazolyzo)-p-cresol, porphyrin compounds, 2-(5-bromo-2-pyridylazo)-5-(diethylamino)phenol, 7-dimethylamino-4-hydroxy-3-oxo-phenoxazine-1-carboxylic acid (gallocynine), titanium dioxide, or combinations thereof. A concentration of lead in the fluid may be correlated to an absorption intensity of electromagnetic radiation absorbed by a sensor including such optically sensitive materials.

In other embodiments, a pH of a fluid may be estimated with a sensor 200 including optically sensitive materials 202 selected from the group consisting of gold nanoparticles, and one or more of a plurality of pH dyes (e.g., malachite green, thymol blue, methyl yellow, methyl red, methyl purple, phenol red, cresol red, rhodamine B, bromophenol blue, etc.) in a matrix material 204. Responsive to exposure to the fluid, an optical absorbance of electromagnetic radiation through the sensor 200 including such optically sensitive materials 202 may change. A pH of the fluid may be estimated based on the optical absorbance of electromagnetic radiation through the sensor 200 when the sensor is exposed to the fluid.

Figure 4:
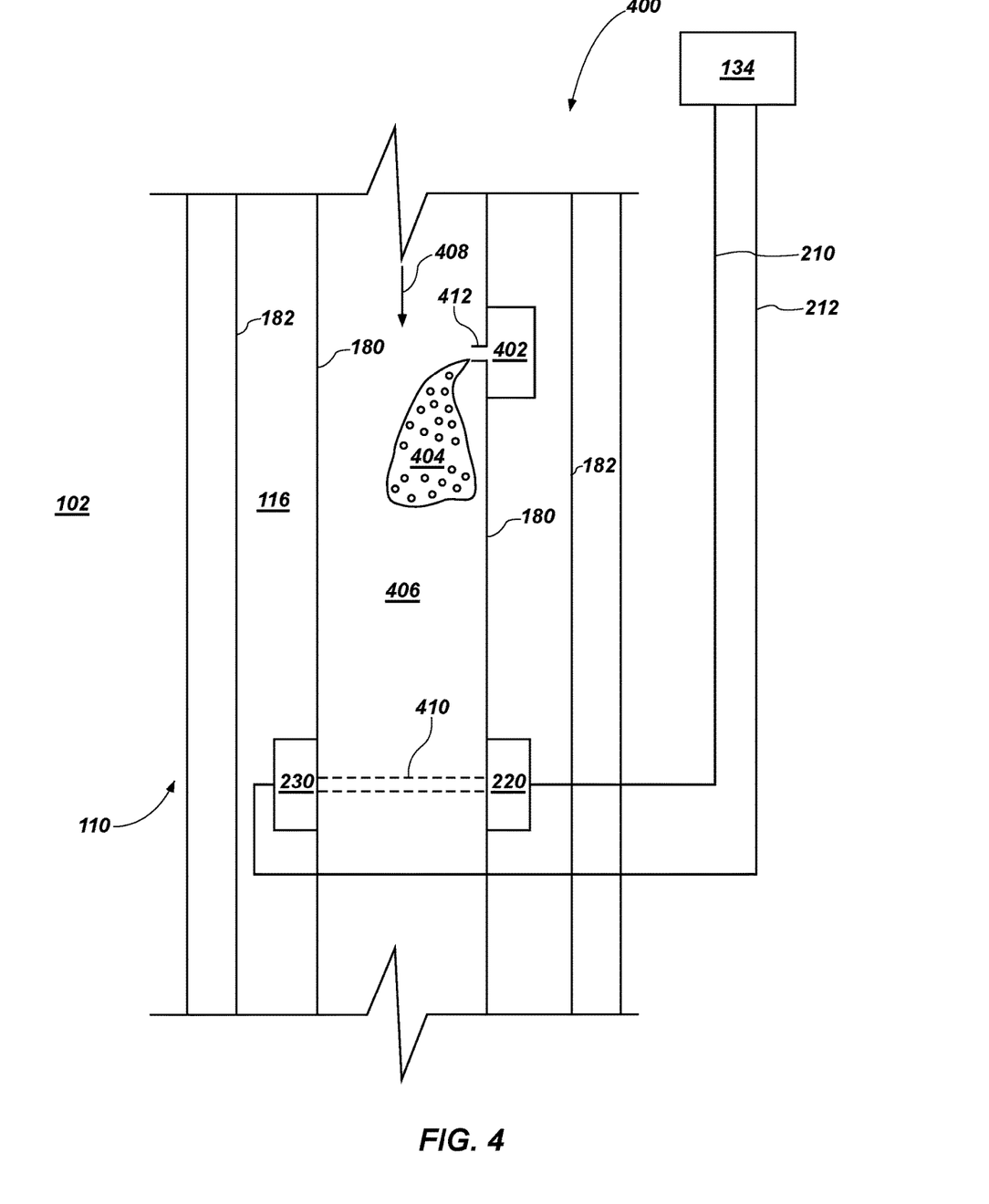
FIG. 4 is a simplified schematic of a chemical delivery system and optical sensor assembly according to an embodiment of the disclosure.

In other embodiments, a concentration of one or more analytes or conditions of the fluid may be estimated by introducing one or more of the optically sensitive materials 202 into the wellbore 110 (FIG. 1), such as in the drill string 116 or in a production string. FIG. 4 is a simplified schematic of a portion of a drill string 116 (FIG. 1) including a fluid injection system 400 according to an embodiment of the disclosure. The fluid injection system 400 may include the radiation source 220 configured to transmit electromagnetic radiation through a wellbore fluid 406 and the detector 230 configured to measure one or more properties of the electromagnetic radiation transmitted through the wellbore fluid 406. The fluid injection system 400 includes a fluid delivery system 402, including an injection port 412, configured and positioned to deliver an optically sensitive fluid 404 including one or more types of optically sensitive materials into the wellbore, such as into the drill string 116. The optically sensitive fluid 404 may include one or more of the optically sensitive materials 202 described above with reference to FIG. 3. A wellbore fluid 406 may flow in the drill string 116 in the direction indicated by arrow 408. The wellbore fluid 406 may carry the optically sensitive fluid 404 to a location proximate the radiation source 220 and the detector 230, which may be located downstream from the fluid delivery system 402. The optically sensitive fluid 404 may substantially mix with the wellbore fluid 406 prior to being exposed to electromagnetic radiation 410 from the radiation source 220.

The optically sensitive materials in the optically sensitive fluid 404 may interact with (e.g., react with) components within the wellbore fluid 406. Responsive to exposure to the electromagnetic radiation 410, the optically sensitive materials may exhibit one or more optical properties that may be received by the detector 230, which, in some embodiments, may be located directly across from the radiation source 220. In other embodiments, the detector 230 may be located adjacent the radiation source 220, such that the optically sensitive materials pass the detector 230 directly after exposure to the electromagnetic radiation 410. Accordingly, a concentration of an analyte within the wellbore fluid 406 or a condition of the wellbore fluid 406 may be determined by disposing the optically sensitive materials into the wellbore fluid 406 (e.g., via the optically sensitive fluid 404) and detecting at least one optical property of the resulting fluid passing by the radiation source 220 and the detector 230.

Although not show in FIG. 4 for clarity, the optical fiber 210 and the another optical fiber 212 may extend within the drill string 116, such as between the inner wall 180 and the outer wall 182. In some embodiments, radiation source 220, the detector 230, the optical fiber 210, and the another optical fiber 212 may be powered by a power sub that may comprise a part of the drill string 116.

In some embodiments, the detector 230 may be configured to transmit information about the detected optical properties to the surface 104 (FIG. 1) (e.g., to the surface control unit 134), such as by, for example, the another optical fiber 212 coupled to the detector 230, by mud pulse telemetry, by a wired connection extending through drill pipe wall, or by other conventional uplink/downlink apparatus. The surface control unit 134 may include a processor and a memory configured to store information related to a correlation between the at least one optical property and a concentration of an analyte in the fluid or a condition of the fluid. Responsive to receiving information about the at least one optical property from the detector 230, the surface control unit 134 may estimate a concentration of at least one analyte in the wellbore fluid, a condition of the wellbore fluid, or a combination thereof.

EXAMPLES

Example 1

Optical Absorbance Spectra of Nitrobenzofurazan Solutions with Different Concentrations of Sodium Sulfide The optical absorbance spectra of a plurality of solutions including nitrobenzofurazan (e.g., chloronitrobenzofurazan) and sodium sulfide were measured with a spectrophotometer to measure a relationship between an absorption intensity and a concentration of sulfide ions in a solution. Hydrogen sulfide dissolved in wellbore fluids may exhibit similar properties to the sulfide ions that were dispersed in each of the solutions. An amount of sodium sulfide present in each solution correlated to the absorption intensity of each respective solution. Accordingly, a concentration of hydrogen sulfide in a wellbore fluid may be correlated to an absorption intensity of electromagnetic radiation passing through a sensor including the nitrobenzofurazan.

Figure 5A:
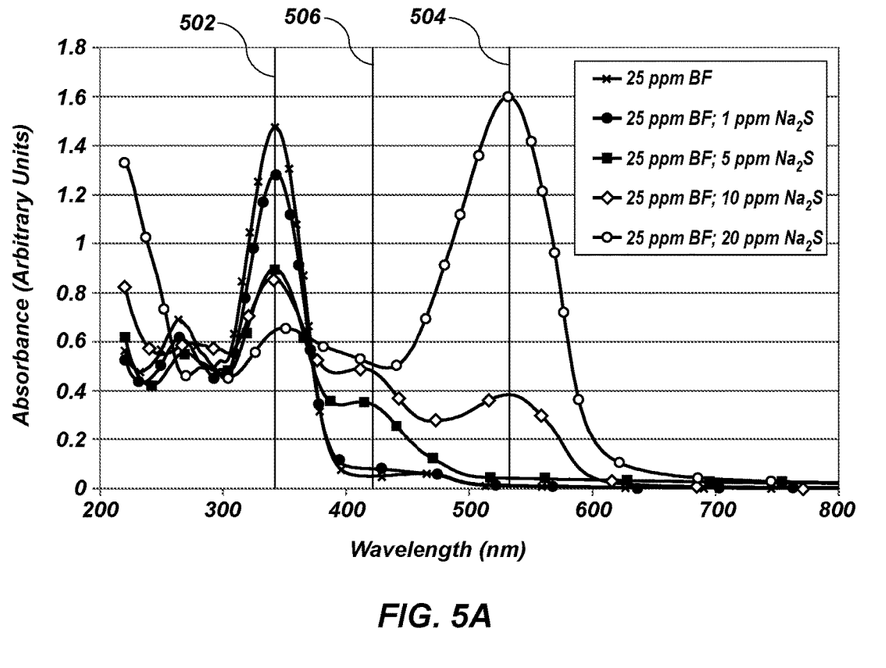
FIG. 5A is an absorbance spectrum of a solution including nitrobenzofurazan and sodium sulfide.

FIG. 5A is an absorption spectrum of a plurality of solutions including different amounts of sodium sulfide ($Na_2S$) and 25 ppm nitrobenzofurazan ("BF"). A first solution did not include any sodium sulfide, while the other solutions included 1 ppm, 5 ppm, 10 ppm, and 20 ppm sodium sulfide. An absorption intensity at a wavelength of about 342 nm, indicated at line 502, may correspond to the amount of nitrobenzofurazan in the solution. An absorption intensity at a wavelength of about 532 nm, indicated at line 504, may correspond to a reaction product of dissolved sulfide from the solution and the nitrobenzofurazan. An absorption intensity at a wavelength of about 420 nm, indicated at line 506, may correspond to an intermediate reaction product of a reaction between the nitrobenzofurazan and the sodium sulfide. As the concentration of sodium sulfide in the solution increased, the absorbance at a wavelength of about 532 nm increased. For example, at a sodium sulfide concentration of 0 ppm and 1 ppm, the absorbance at 532 nm appeared to be negligible. When the sodium sulfide concentration was increased to 5 ppm, the absorbance increased slightly. At 10 ppm and 20 ppm, the absorption intensity increased significantly. Without wishing to be bound by any particular theory, it is believed that the sulfide reacts with the nitrobenzofurazan and forms a reaction product exhibiting an optical absorbance at a wavelength of about 532 nm.

As more sodium sulfide reacted with the nitrobenzofurazan, an absorption intensity at a wavelength of about 342 nm decreased, indicating that the nitrobenzofurazan was reacting with, and being consumed by, the sulfide.

An absorption intensity at a wavelength of about 420 nm increased with an increasing concentration of sodium sulfide. It is believed that the increased absorption intensity at a wavelength of about 420 nm corresponds to an intermediate reaction product of the reaction between the nitrobenzofurazan and the sodium sulfide.

Figure 5B:
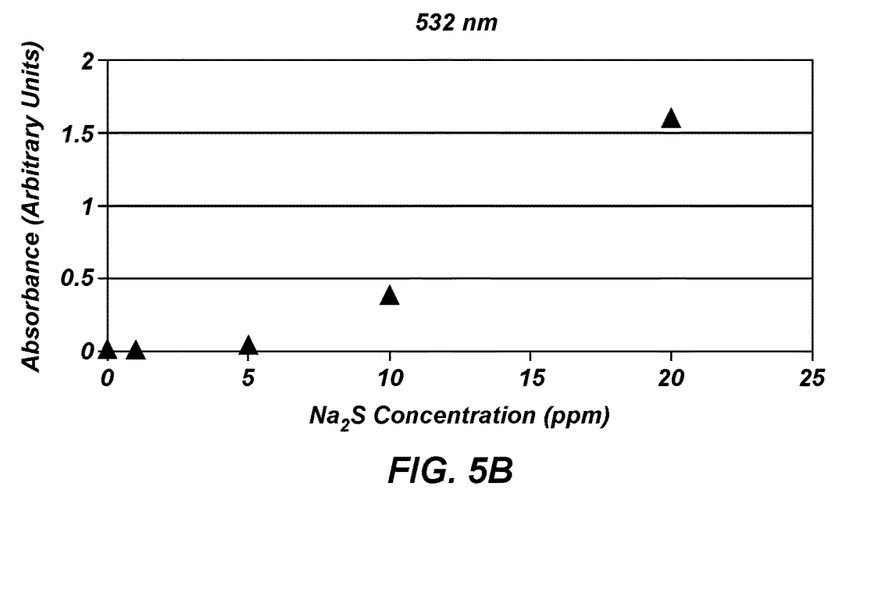
FIG. 5B is a graph illustrating a relationship between an absorption intensity and a concentration of sodium sulfide in a solution.

FIG. 5B is a graph illustrating a relationship between an absorption intensity of electromagnetic radiation absorbed by a sensor including nitrobenzofurazan dispersed in a silica matrix and a concentration of sodium sulfide in a fluid to which the sensor was exposed. As the concentration of sodium sulfide in the fluid increased, the absorption intensity of electromagnetic radiation passing through the sensor increased. It is believed that the nitrobenzofurazan reacts with hydrogen sulfide in a manner similar to that of the reaction between nitrobenzofurazan and sodium sulfide.

Example 2

Figure 6:
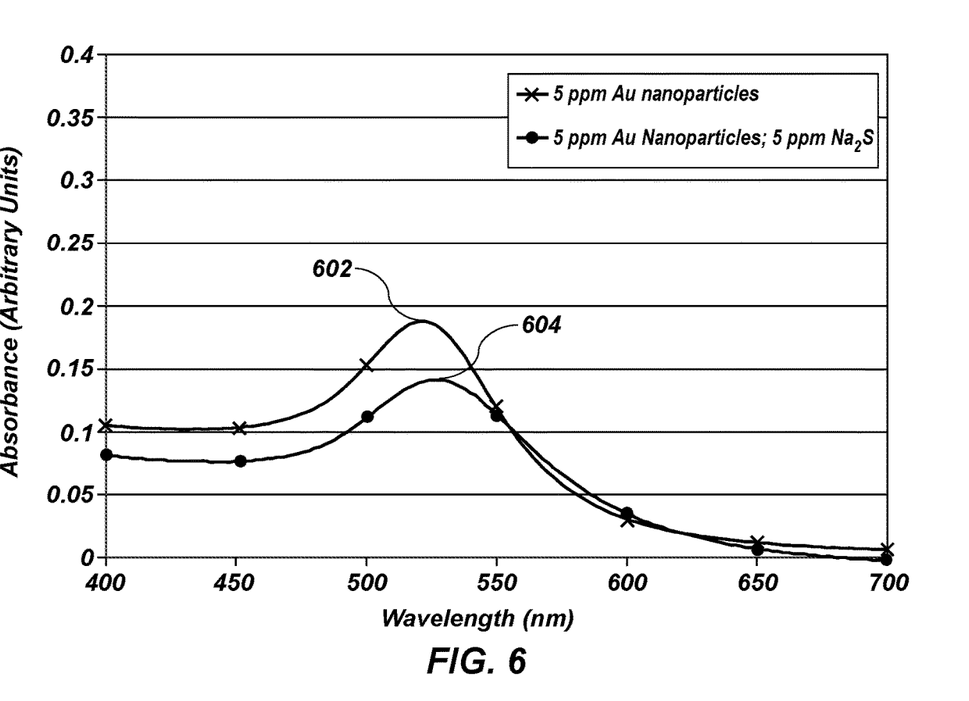
FIG. 6 is an absorbance spectrum of a solution including gold nanoparticles in sodium sulfide solution.

Optical Absorbance Spectrum of Au—$SiO_2$ Nanocomposite Before and after Exposure to 5 ppm Sodium Sulfide FIG. 6 is a graph showing an absorbance spectrum of electromagnetic radiation through a sensor including gold nanoparticles dispersed within a silica matrix material before and after exposure to a solution including about 5 ppm of sodium sulfide. As indicated at 602, when there was no sodium sulfide in the solution, the peak absorption wavelength was about 522 nm. When the solution included about 5 ppm sodium sulfide, the peak absorption intensity shifted to about 528 nm, as indicated at 604. It is believed that as the concentration of sodium sulfide in the fluid increases, the peak optical absorbance wavelength shifts from about 522 nm with increasing wavelengths, depending on a concentration of sulfide in the solution (e.g., at about 5 ppm sulfide, the peak absorption wavelength is about 528 nm and at a higher sulfide concentration, the peak absorption wavelength would be higher). It is believed that the sodium sulfide physically adsorbs onto surfaces of the sensor, shifting the optical absorbance of the sensor. Accordingly, a concentration of hydrogen sulfide in a fluid may be estimated by measuring a wavelength of a peak absorption intensity of electromagnetic radiation through the sensor.

Additional nonlimiting example embodiments of the disclosure are described below.

Embodiment 1

A method of detecting at least one of an analyte or a condition of a fluid within a subterranean formation, the method comprising: operably coupling a radiation source to at least one optical fiber coupled to a sensor comprising optically sensitive materials including at least one of chromophores, fluorophores, metal nanoparticles, or metal oxide nanoparticles dispersed within an optically transparent permeable matrix material; contacting the sensor within a wellbore with a fluid and passing the fluid through at least a portion of the sensor comprising the optically sensitive materials; transmitting electromagnetic radiation from the radiation source through at least one optical fiber to the sensor; and measuring at least one of an absorbance spectrum, an emission spectrum, a maximum absorption intensity, or a maximum emission intensity of electromagnetic radiation passing through the sensor after contacting at least some of the optically sensitive materials with the fluid.

Embodiment 2

The method of Embodiment 1, wherein contacting the sensor within a wellbore with a fluid and passing the fluid through at least a portion of the sensor comprising the optically sensitive materials comprises one of physical absorbing an analyte within the fluid to the optically sensitive materials or chemically reacting the optically sensitive materials with the analyte.

Embodiment 3

The method of Embodiment 1 or Embodiment 2, wherein measuring at least one of an absorbance spectrum, an emission spectrum, a maximum absorption intensity, or a maximum emission intensity of electromagnetic radiation passing through the sensor comprises measuring a wavelength of maximum absorption intensity of the electromagnetic radiation passing through the sensor.

Embodiment 4

The method of any one of Embodiments 1 through 3, further comprising: selecting the optically sensitive materials to comprise chromophores; and chemically reacting at least some of the chromophores within the sensor with an analyte within the fluid.

Embodiment 5

The method of any one of Embodiments 1 through 4, further comprising determining a concentration of hydrogen sulfide in the fluid based on at least one of a measured absorbance spectrum, emission spectrum, maximum absorption intensity, or maximum emission intensity of the electromagnetic radiation passing through the sensor after contacting at least some of the optically sensitive materials with the fluid.

Embodiment 6

The method of any one of Embodiments 1 through 5, further comprising selecting the optically sensitive materials to comprise rhodamine B, a copper (II) chromophore complex, copper nanoparticles, 2,6-dichlorophenolindophenol, chloronitrobenzofurazan, or m-bromobiamine.

Embodiment 7

The method of any one of Embodiments 1 through 3, or 5, further comprising selecting the optically sensitive materials to comprise nanoparticles of at least one of gold, silver, palladium, or platinum.

Embodiment 8

The method of any one of Embodiments 1 through 7, selecting the optically sensitive materials to comprise at least one of zinc oxide, cadmium oxide, tungsten oxide, or combinations thereof.

Embodiment 9

The method of any one of Embodiments 1 through 8, further comprising selecting the optically transparent permeable matrix material to comprise a porous glass.

Embodiment 10

The method of any one of Embodiments 1 through 8, further comprising selecting the optically transparent permeable matrix material to comprise at least one of polyvinylidene chloride, a polyether, a polyacrylate, or a polysilicone.

Embodiment 11

A method of determining a concentration of hydrogen sulfide in a fluid within a subterranean formation, the method comprising: locating a sensor comprising optically sensitive materials comprising at least one of chromophores, fluorophores, and nanoparticles dispersed within a permeable matrix material proximate at least one component of downhole equipment in a wellbore extending through one or more subterranean formations, the sensor operably coupled through at least one fiber optic cable to a radiation source configured to provide electromagnetic radiation to the sensor; contacting the sensor with a fluid within at least one of the downhole equipment or the wellbore; transmitting electromagnetic radiation from the radiation source through the sensor and to a detector operably coupled to the at least one fiber optic cable; and determining, with the detector, a change in an optical characteristic of at least one of the optically sensitive materials of the sensor responsive to contact of the sensor with the fluid.

Embodiment 12

The method of Embodiment 11, further comprising selecting the optically sensitive materials to comprise nanoparticles of at least one of gold, silver, palladium, platinum, or copper dispersed within the permeable matrix material.

Embodiment 13

The method of Embodiment 11 or Embodiment 12, further comprising selecting the optically sensitive materials to comprise metal oxide nanoparticles dispersed within the permeable matrix material.

Embodiment 14

The method of Embodiment 13, further comprising selecting the metal oxide nanoparticles to comprise at least one of zinc oxide, tungsten oxide, cadmium oxide, or iron oxides.

Embodiment 15

The method of any one of Embodiments 11 through 14, further comprising selecting the optically sensitive materials to comprise rhodamine B, a copper (II) chromophore complex, copper nanoparticles, 2,6-dichlorophenolindophenol, chloronitrobenzofurazan, or m-bromobiamine.

Embodiment 16

The method of any one of Embodiments 11 through 15, further comprising selecting the optically sensitive materials to comprise a material selected from the group consisting of p-azidophenylalanine, rhodamine, dansyl azide, and dicyanomethylenedihydrofuran.

Embodiment 17

A downhole optical sensor assembly, comprising: a sensor operably coupled to at least one component of downhole equipment, the sensor including optically sensitive materials comprising one of chromophores, fluorophores, metal nanoparticles, or metal oxide nanoparticles disposed within a permeable optically transparent matrix material; a radiation source coupled to the sensor through a fiber optic cable, the radiation source configured to generate electromagnetic radiation for transmission through at least one optical fiber of the fiber optic cable; and a detector coupled to the sensor through a fiber optic cable, the detector configured to measure at least one of an absorbance spectrum, an emission spectrum, a maximum absorption intensity, or a maximum emission intensity of electromagnetic radiation passing through the sensor.

Embodiment 18

The downhole optical sensor assembly of Embodiment 17, wherein the optically sensitive materials comprise nanoparticles of at least one of gold, silver, palladium, platinum, or copper.

Embodiment 19

The downhole optical sensor assembly of Embodiment 17 or Embodiment 18, wherein the optically sensitive materials comprise: at least one of rhodamine B, a copper (II) chromophore complex, copper nanoparticles, 2,6-dichlorophenolindophenol, chloronitrobenzofurazan, or m-bromobiamine; and at least one of gold, silver, platinum, palladium, zinc oxide, cadmium oxide, or tungsten oxide.

Embodiment 20

The downhole optical sensor assembly of any one of Embodiments 17 through 19, wherein the sensor comprises at least one chromophore, at least one fluorophore, and at least one metal nanoparticle.

While the disclosure is susceptible to various modifications and alternative forms, specific embodiments have been shown by way of example in the drawings and have been described in detail herein. However, the disclosure is not intended to be limited to the particular forms disclosed. Rather, the disclosure is to cover all modifications, equivalents, and alternatives falling within the scope of the disclosure as defined by the following appended claims and their legal equivalents.

What is claimed is:

1. A method of detecting at least one of an analyte or a condition of a downhole fluid within a subterranean formation, the method comprising:
    operably coupling a radiation source to at least one optical fiber coupled to a sensor comprising optically sensitive materials including at least one of chromophores, fluorophores, metal nanoparticles, or metal oxide nanoparticles dispersed within an optically transparent matrix material permeable to a downhole fluid in a wellbore;
    contacting the sensor within the wellbore with the downhole fluid and gases dissolved therein and passing both the downhole fluid and gases dissolved therein through at least a portion of the sensor comprising the optically sensitive materials;
    transmitting electromagnetic radiation from the radiation source through the at least one optical fiber to the sensor; and
    measuring at least one of an absorbance spectrum, an emission spectrum, a maximum absorption intensity, or a maximum emission intensity of electromagnetic radiation passing through the sensor after contacting at least some of the optically sensitive materials with the downhole fluid.

2. The method of claim 1, wherein contacting the sensor within the wellbore with the downhole fluid and passing the downhole fluid through at least a portion of the sensor comprising the optically sensitive materials comprises one of physical absorbing an analyte within the downhole fluid to the optically sensitive materials or chemically reacting the optically sensitive materials with the analyte.

3. The method of claim 1, wherein measuring at least one of an absorbance spectrum, an emission spectrum, a maximum absorption intensity, or a maximum emission intensity of electromagnetic radiation passing through the sensor comprises measuring a wavelength of maximum absorption intensity of the electromagnetic radiation passing through the sensor.

4. The method of claim 3, further comprising:
    selecting the optically sensitive materials to comprise chromophores; and
    chemically reacting at least some of the chromophores within the sensor with an analyte within the downhole fluid.

5. The method of claim 1, further comprising determining a concentration of hydrogen sulfide in the downhole fluid based on at least one of a measured absorbance spectrum, emission spectrum, maximum absorption intensity, or maximum emission intensity of the electromagnetic radiation passing through the sensor after contacting at least some of the optically sensitive materials with the downhole fluid.

6. The method of claim 1, further comprising selecting the optically sensitive materials to comprise rhodamine B, copper nanoparticles, chloronitrobenzofurazan, or m-bromobiamine.

7. The method of claim 1, further comprising selecting the optically sensitive materials to comprise nanoparticles of at least one of gold, silver, palladium, or platinum.

8. The method of claim 1, further comprising selecting the optically sensitive materials to comprise at least one of zinc oxide, cadmium oxide, tungsten oxide, or combinations thereof.

9. The method of claim 1, further comprising selecting the optically transparent permeable matrix material to comprise a porous glass.

10. The method of claim 1, further comprising selecting the optically transparent permeable matrix material to comprise at least one of polyvinylidene chloride, a polyether, a polyacrylate, or a polysilicone.

11. A method of determining a concentration of hydrogen sulfide in a downhole fluid within a subterranean formation, the method comprising:
    locating a sensor comprising optically sensitive materials comprising at least one of chromophores, fluorophores, and nanoparticles dispersed within a permeable matrix material permeable to a downhole fluid proximate at least one component of downhole equipment in a wellbore extending through one or more subterranean formations, the sensor operably coupled through at least one fiber optic cable to a radiation source configured to provide electromagnetic radiation to the sensor;
    contacting the sensor with the downhole fluid and gases dissolved therein within at least one of the downhole equipment or the wellbore and passing both the downhole fluid and gases dissolved therein through at least a portion of the sensor comprising the optically sensitive materials;

transmitting electromagnetic radiation from the radiation source through the sensor and to a detector operably coupled to the at least one fiber optic cable; and determining, with the detector, a change in an optical characteristic of at least one of the optically sensitive materials of the sensor responsive to contact of the sensor with hydrogen sulfide in the downhole fluid.

12. The method of claim 11, further comprising selecting the optically sensitive materials to comprise nanoparticles of at least one of gold, silver, palladium, platinum, or copper dispersed within the permeable matrix material.

13. The method of claim 11, further comprising selecting the optically sensitive materials to comprise metal oxide nanoparticles dispersed within the permeable matrix material.

14. The method of claim 13, further comprising selecting the metal oxide nanoparticles to comprise at least one of zinc oxide, tungsten oxide, cadmium oxide, or iron oxides.

15. The method of claim 11, further comprising selecting the optically sensitive materials to comprise rhodamine B, a copper (II) chromophore complex, copper nanoparticles, 2,6-dichlorophenolindophenol, chloronitrobenzofurazan, or m-bromobiamine.

16. The method of claim 11, further comprising selecting the optically sensitive materials to comprise a material selected from the group consisting of p-azidophenylalanine, rhodamine, dansyl azide, and dicyanomethylenedihydrofuran.

17. A downhole optical sensor assembly, comprising:
a sensor operably coupled to at least one component of downhole equipment, the sensor including optically sensitive materials comprising one of chromophores, fluorophores, metal nanoparticles, or metal oxide nanoparticles disposed within an optically transparent matrix material permeable to a downhole fluid;

a radiation source coupled to the sensor through a fiber optic cable, the radiation source configured to generate electromagnetic radiation for transmission through at least one optical fiber of the fiber optic cable; and a detector coupled to the sensor through a fiber optic cable, the detector configured to measure at least one of an absorbance spectrum, an emission spectrum, a maximum absorption intensity, or a maximum emission intensity of electromagnetic radiation passing through the sensor.

18. The downhole optical sensor of claim 17, wherein the optically sensitive materials comprise nanoparticles of at least one of gold, silver, palladium, platinum, or copper as a result of both the downhole fluid and gases dissolved therein passing through at least a portion of the sensor comprising the optically sensitive materials.

19. The downhole optical sensor assembly of claim 17, wherein the optically sensitive materials comprise:
at least one of rhodamine B, a copper (II) chromophore complex, copper nanoparticles, 2,6-dichlorophenolindophenol, chloronitrobenzofurazan, or m-bromobiamine; and at least one of gold, silver, platinum, palladium, zinc oxide, cadmium oxide, or tungsten oxide.

20. The downhole optical sensor assembly of claim 17, wherein the sensor comprises at least one chromophore, at least one fluorophore, and at least one metal nanoparticle.

* * * * *

UNITED STATES PATENT AND TRADEMARK OFFICE
CERTIFICATE OF CORRECTION

Page 1 of 1

PATENT NO. : 10,025,000 B2
APPLICATION NO. : 15/003578
DATED : July 17, 2018
INVENTOR(S) : Othon R. Monteiro and Radhika Suresh It is certified that error appears in the above-identified patent and that said Letters Patent is hereby corrected as shown below:

In the Claims

Claim 17, Column 20, Line 13, change "the sensor." to --the sensor as a result of both the downhole fluid and gases dissolved therein passing through at least a portion of the sensor comprising the optically sensitive materials.--

Claim 18, Column 20, Lines 16-19, change "or copper as a result of both the downhole fluid and gases dissolved therein passing through at least a portion of the sensor comprising the optically sensitive materials." to --or copper.--

Signed and Sealed this
Twenty-fifth Day of September, 2018

Andrei Iancu
*Director of the United States Patent and Trademark Office*